(12) United States Patent
Crell

(10) Patent No.: US 6,970,589 B2
(45) Date of Patent: Nov. 29, 2005

(54) METHOD FOR INSPECTING DEFECTS ON A MASK

(75) Inventor: Christian Crell, Forstinning (DE)

(73) Assignee: Infineon Technologies AG, Munich (DE)

(*) Notice: Subject to any disclaimer, the term of this patent is extended or adjusted under 35 U.S.C. 154(b) by 703 days.

(21) Appl. No.: 10/060,450

(22) Filed: Jan. 30, 2002

(65) Prior Publication Data

US 2002/0103607 A1 Aug. 1, 2002

(30) Foreign Application Priority Data

Jan. 30, 2001 (DE) ................. 101 03 958

(51) Int. Cl.[7] .............................................. G06K 9/00
(52) U.S. Cl. .................................... 382/144; 382/145
(58) Field of Search ....................... 382/141, 144–149, 382/209, 217, 218, 224; 716/19, 21

(56) References Cited

U.S. PATENT DOCUMENTS

| | | | | |
|---|---|---|---|---|
| 5,253,306 A | * | 10/1993 | Nishio | ................. 382/112 |
| 5,650,854 A | * | 7/1997 | Sugawara | ............... 356/394 |
| 5,767,974 A | * | 6/1998 | Higashiguchi et al. | ...... 356/394 |
| 6,002,791 A | * | 12/1999 | Okada | ...................... 382/144 |
| 6,043,932 A | | 3/2000 | Kusunose | |

FOREIGN PATENT DOCUMENTS

| | | |
|---|---|---|
| DE | 691 27835 | 7/1991 |
| DE | 196 22 037 A1 | 12/1996 |
| DE | 197 34 486 A1 | 2/1998 |
| EP | 0 532 927 A2 | 3/1993 |

* cited by examiner

Primary Examiner—Vikkram Bali
(74) Attorney, Agent, or Firm—Laurence A. Greenberg; Werner H. Stemer; Ralph E. Locher

(57) ABSTRACT

The whole-area defect inspection of masks is made possible by interconnecting two otherwise independent defect inspection systems via a powerful bus system or interface. As a result, two masks that are identical, at least in sub-areas, can be inspected and compared in parallel and in real time. It is not necessary to temporarily store large quantities of data. The running defect inspection can be interrupted flexibly and continued again. This implementation of mask-to-mask inspection takes into account that simulation algorithms for die-to-database inspection of future mask technology, for example, alternating phase masks, EUV masks, stencil masks, and so on are not available in good time. In addition, the inspection time is reduced considerably.

20 Claims, 3 Drawing Sheets

METHOD FOR INSPECTING DEFECTS ON A MASK

BACKGROUND OF THE INVENTION

Field of the Invention

The present invention relates to a method for inspecting defects on a mask.

With the constant reduction in minimum structure sizes and the associated, resolution-induced change from optical to non-optical wavelengths during the exposure of semiconductor products, new requirements are also being placed on the minimum structure sizes and on the functional modes of the masks that are needed to structure the wafers. The conventional technique that is used in the exposure step to copy the structure present on the mask in a reduced form or at the same size onto the wafer includes using the optical exposure of the diffraction or the phase properties of the light that is applied during the development of so-called half-tone, alternating and 3-tone phase masks.

During the implementation of these measures on the mask, zones of a third or further type of transparency are structured to achieve higher resolutions on the exposed wafer. By using optical proximity correction (OPC) on the mask, additional artificial structures are also applied that serve merely to compensate for inherent errors in the exposure of the wafer and to bring the exposed structure as close as possible to the data image again.

In recent times, masks for non-optically transferring structures to wafers have also been developed, including those in which radiation is reflected in the extreme ultraviolet range (EUV), and stencil masks, in which the structures are transferred using electron beams or ion beams. Presently, these masks are mostly membrane masks produced from silicon wafers, as opposed to the quartz plates previously used as the basis for masks.

With the increased requirements placed on the lithographic techniques, steps are also needed for defect inspection, which must be managed. First, defects of an even smaller size have to be traced, and second because of the broader range of mask types, it is increasingly also necessary to account for the structural differences between the structure that is applied to the mask and the image achieved on the wafer. As a result of the considerable increases in the speed of computing systems in recent years, changes have increasingly been made from the conventional die-to-die inspection in which identical structures present many times on the mask are compared with one another to die-to-database inspection in which a structure on the mask is compared with a data image stored in the database.

In the case of die-to-database inspection—to make a comparison possible—an algorithm is used to convert the data image from the database into an image that simulates the optical characteristics of the mask transfer. The more complex the optical structure to be transferred, for example, phase-shifted signals or OPC structures, the more time-consuming the inspection becomes, and also the more difficult the development of an underlying algorithm becomes.

If, for conventional chrome-on-glass masks, OPC structures and half-tone phase masks, satisfactory solutions for the algorithms could be delivered within an adequate time interval following the delivery of newly developed types of defect inspection systems, then for the alternating phase masks, the 3-tone face masks, the EUV and stencil masks found in development, the problem arises that the algorithms for the reconstruction of a mask image from its data image will no longer be obtainable in good time. To generate masks with electron-optical or ion-optical characteristics, it is forecast that this effect will emerge to a particularly considerable extent.

One way around the problem would be recourse to die-to-die inspection, which is still being used, but because of the frequently singular structures on the masks, is not always possible. The advantage here would be that the mask image would not have to be simulated. Modern defect inspection systems are designed to store extremely small areas on the mask temporarily in order to then change the coordinates of the reference die, to find the corresponding matching piece of the structure, and to compare the current image with the image temporarily stored.

The same procedure would be possible in the case of mask-to-mask inspection in which the structures of two identical masks are inspected one after another. The image from the first mask is stored temporarily, and during the inspection of the second mask, is compared with the image of the second mask. Unfortunately in this case, the considerable disadvantage arises that retrieving the stored data out of memory is too time-consuming, and that memories in the order of magnitude of some terabytes would be needed which are rarely available at the present time. In addition, it is often the case that necessary interruptions in the inspection cannot readily be carried out.

U.S. Pat. No. 6,043,932 shows an inspection instrument for die-to-die inspection in which, by splitting the laser beam and subsequently adjusting the partial beams onto the individual dies, and by recording the die structures in parallel with a linear image sensor, a comparison of the images is enabled in real time. However, the aforementioned disadvantages also arise here, that the method is restricted to non-singular mask structures and that the respective partial beam optics can only be of small size.

SUMMARY OF THE INVENTION

It is accordingly an object of the invention to provide a method for inspecting defects on a mask which overcomes the above-mentioned disadvantages of the prior art methods of this general type.

In particular, it is an object of the invention to provide, irrespective of the mask technology used, whole-area defect inspection of masks—even of masks with singular structures, to ensure a higher quality of the masks, and to permit accelerated mask inspection.

With the foregoing and other objects in view there is provided, in accordance with the invention, a method for inspecting defects on a mask, that includes steps of: (a) loading a first defect inspection system with a first mask having a surface with at least a sub-area having structuring; (b) loading a second defect inspection system with a reference mask having a surface with at least a sub-area having structuring that is identical to the structuring of the sub-area of the first mask; (c) connecting a bus system between a first control computer belonging to the first defect inspection system and a second control computer belonging to the second defect inspection system and using the bus system to communicate between the first control computer and the second control computer; (d) using the first defect inspection system to record a portion of the sub-area of the first mask and using the first control computer to construct a first image from the portion; (e) using the second defect inspection system to record a portion of the sub-area of the reference mask and using the second control computer to construct a second image from the portion of the reference mask; (f) using the bus system to perform an operation selected from the group consisting of transferring the first image from the first control computer to the second control computer and transferring the second image from the second control computer to the first control computer; (g) comparing the first image with the second image; and (h) classifying the first mask based on a result of the comparing step.

In accordance with an added feature of the invention, after step (g), steps (d), (e) and (f) are repeated to record further portions of the sub-area of the first mask and of the sub-area of the reference mask.

In accordance with an additional feature of the invention, the first mask is inspected while the reference mask is inspected.

In accordance with another feature of the invention, step (g) is carried out while using the first defect inspection system to record another portion of the sub-area of the first mask and using the first control computer to construct a first image from the other portion, and while using the second defect inspection system to record another portion of the sub-area of the reference mask and using the second control computer to construct a second image from the other portion of the reference mask.

In accordance with a further added feature of the invention, the first mask is a mask structured on a silicon wafer and the reference mask is a mask structured on a silicon wafer.

In accordance with a further additional feature of the invention, the first mask is either a mask structured on a silicon wafer or a mask structured on quartz plate with a reflective coating; and the reference mask is either a mask structured on a silicon wafer or a mask structured on quartz plate with a reflective coating.

In accordance with yet an added feature of the invention, control signals are output from either the first control computer or the second control computer to control both the first defect inspection system and the second defect inspection system.

In accordance with yet an additional feature of the invention, a bus system providing communication is used to connect at least a third control computer to the first control computer and to the second control computer.

In accordance with yet another feature of the invention, at least a third defect inspection system is connected to the third control computer; and the third defect inspection system is loaded with a mask for inspection.

In accordance with the invention, a first mask is inspected in a first defect inspection system by comparing the first mask with a reference mask that is in a second defect inspection system. These two defect inspection systems or their control computers are interconnected. The reference mask and the mask that will be inspected (the first mask) have at least some structures that are identical. A bus system or an interface connects the two control computers. This bus system or interface supplies a sufficiently high data throughput per unit time which, ideally, is approximately as great as that of the connection between the control computer and the defect inspection system. The bandwidth and clock frequency of the data bus system or interface must therefore correspond to this data throughput, but otherwise can be selected as desired.

As a result of this interconnection, the image data recorded, for example, from the reference mask, can be transferred in real time to the control computer controlling the defect inspection system of the mask to be examined. Therefore, the comparative data for a portion to be inspected on the mask are therefore available immediately without temporary storage so that no time has to be expended for the storage, re-finding and reloading of the reference data. The image data, which are available in real time, that is to say in the time needed for scanning the surface structure of the mask, can then be evaluated immediately by one of the two control computers or by a further computer for image evaluation, that is to say the image comparison. For this purpose, conventional inspection or image processing programs can be used. Therefore, by interconnecting two different defect inspection systems, and by comparing at least sub-areas of identical masks, considerably faster inspection can advantageously be achieved. In particular, because image data does not need to be temporarily stored, for example, the data from the reference mask, time is saved.

Ideally, the whole-area defect inspection is carried out by scanning small portions, which are then compared with one another. As a result, in each case, smaller quantities of data are compared. The repetition of these steps on both defect inspection systems then leads to whole-area scanning of the mask. In addition to the advantage that smaller quantities of data can be accommodated conveniently in the main memories of the control computers, without having to use hard drives or other storage media, this also enables the defect inspection systems to be used to record subsequent partial portions as early as during the comparison between the previous partial portions. By using this highly parallel procedure, the inspection is additionally accelerated.

A great advantage results from the fact that the image data that is recorded can be compared directly, in a similar way to that used in die-to-die inspection, without having to read out the image data from the design data of the database and the image data can be processed in a complicated simulation to take into account the EUV and electron-optical characteristics etc. of future or current mask technologies.

In a further refinement, a plurality of defect inspection systems are interconnected to form a cluster. In addition to allowing flexibility in the various systems that can be used, the result in this case is that a reference mask can be used simultaneously for a number of masks that are to be inspected and that are identical, at least in sub-areas. The inspection can therefore, be performed in a manner that saves resources.

A precondition for the implementation of the present method is the presence of a reference mask. The reference mask may be one of a number of identical masks that are produced many times or else can be a mask that has not yet been delivered or that is at an earlier design stage and will be delivered later. At least sub-areas of the reference mask can be used for the comparison. In order to meet the continuously increasing requirements with regard to quality and production time in mask fabrication, however, parallel fabrication of masks is increasingly being used, of which only the first mask meeting the specifications is supplied. However, identical masks that had failed the inspections following previous process steps can be used as a reference mask, taking into account the faults present on them.

Other features which are considered as characteristic for the invention are set forth in the appended claims.

Although the invention is illustrated and described herein as embodied in a method for the inspection of defects on a mask, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following

DESCRIPTION OF THE PREFERRED EMBODIMENTS

Figure 1A:
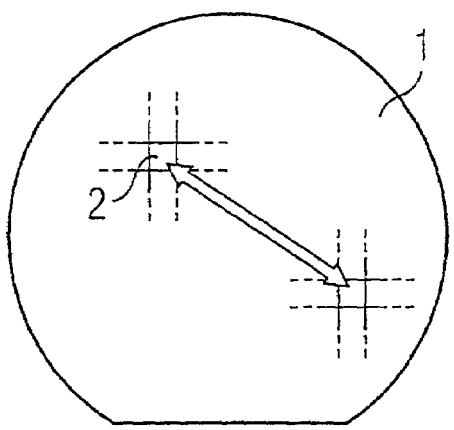
FIG. 1A shows a prior art die-to-die inspection method.
Figure 1B:
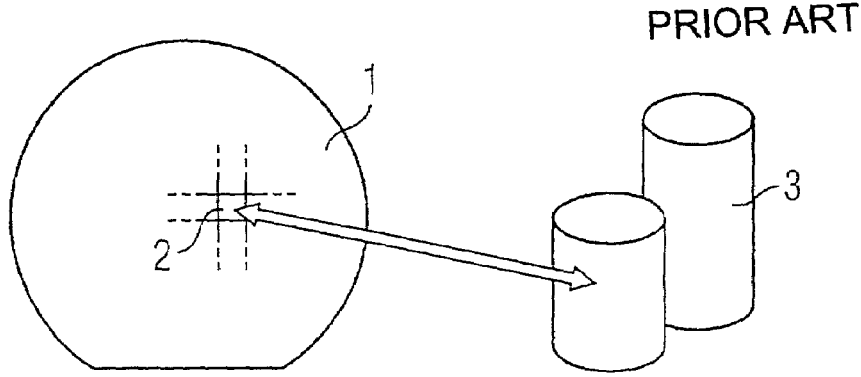
FIG. 1B shows a prior art die-to-database inspection method.

In the following example, the defect inspection is carried out for an alternating phase mask. Referring now to the figures of the drawing in detail and first, particularly, to FIGS. 1A and 1B thereof, prior art methods are shown that are in principle available for the inspection. FIG. 1A shows a sketch of the way in which two dies 2 on a mask 1 are compared with each other, equivalent to die-to-die inspection. FIG. 1B shows a sketch of die-to-database inspection in which the recorded data from the die 2 on the mask 1 is compared with the simulation, taking into account the local phase differences in alternating phase masks. The image data from the database 3 serves as a reference. Since the alternating phase mask 1 in the present example is intended to have a singular structure, the method illustrated in FIG. 1a of comparing two dies on the mask 1 can unfortunately not be used. Because the method of manufacturing the alternating phase mask is still in development, for the die-to-database inspection it is also possible to use only either provisional or in principle inappropriate, conventional simulation algorithms that produce an imaginary reference image from the design data in the database 3 by taking into account the local phase differences and diffraction mechanisms. As a result of these difficulties, first the quality of the defect inspection of the alternating phase mask is influenced detrimentally, and second the simulation duration may greatly exceed the duration required to record the actual image so that the fabrication duration of the mask 1 is disadvantageously prolonged.

Figure 1C:
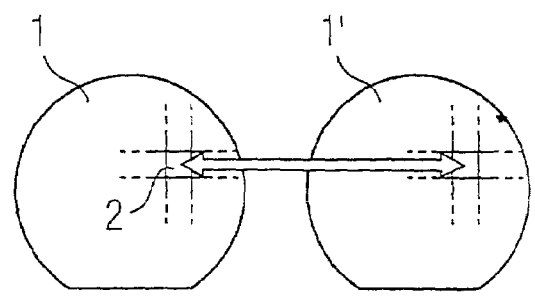
FIG. 1C shows an inventive mask-to-mask inspection method.

If there is a reference mask 1' with a structural image that is identical to the structural image of the mask 1, at least in a sub-area, then corresponding sub-areas of the mask 1 to be examined and the reference mask 1' can be compared with each other, as shown in FIG. 1c, in a similar way to that performed in die-to-die inspection. The difference is that a structure from dies distributed over the mask need not necessarily be present, instead the inspection can be extended to masks with singular structures, that is to say with structures that are present only once on the mask.

Figure 2:
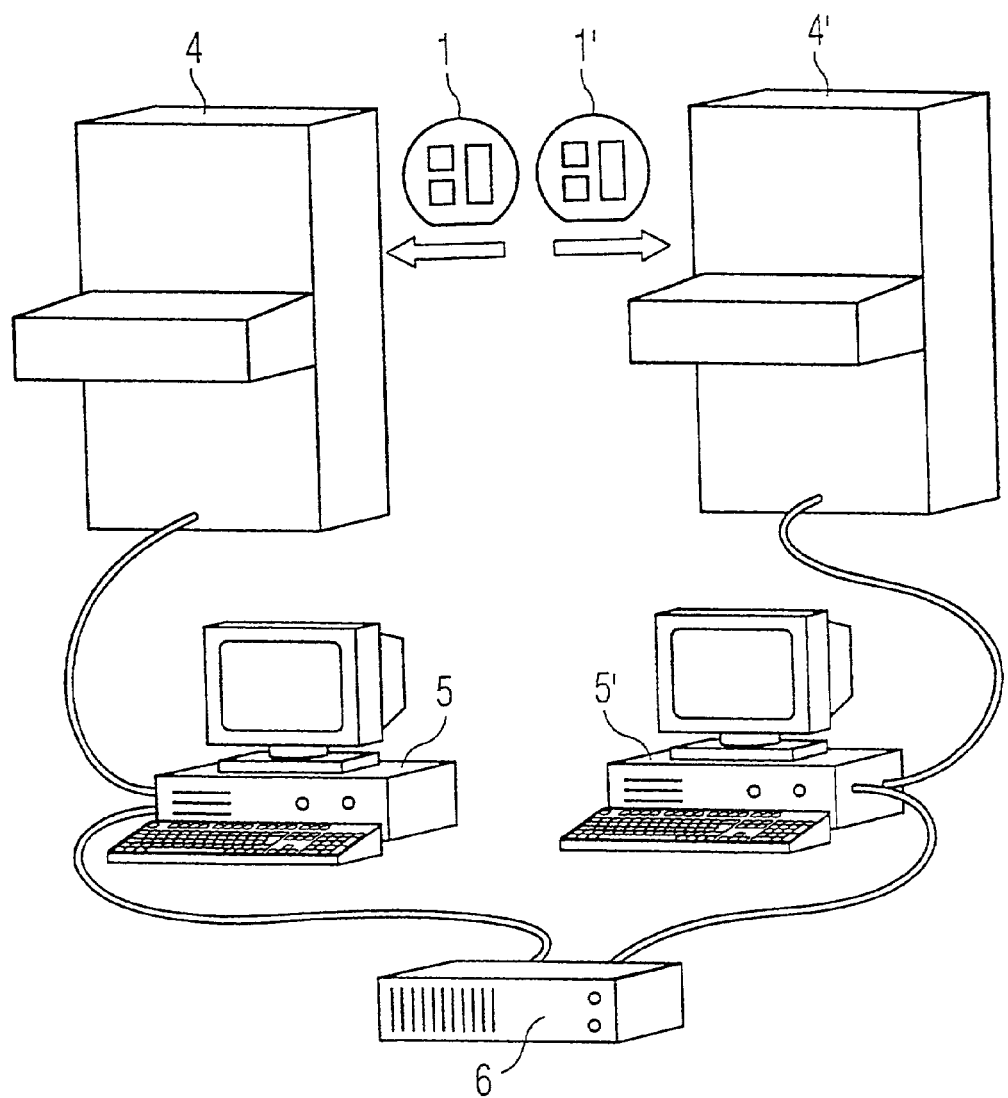
FIG. 2 schematically shows two interconnected defect inspection systems.

In order to implement the defect inspection, two preferably identical defect inspection systems 4, 4', for example KLA 353UV, are respectively loaded with the alternating phase mask 1 that will be examined and with an alternating phase mask 1' that is identical in this example. As illustrated schematically in FIG. 2, the two defect inspection systems 4, 4' are in each case controlled by a control computer 5 and 5', respectively. The two inspection systems 4, 4' are then taken out of the individual operating mode and are connected by an interface 6 that is configured between the two control computers 5 and 5' so that the image data and the control signal can be transferred. The interface 6 provides an approximately equally high data throughput to the control computers 5 and 5' so that the control computers 5 and 5' can manage the respective defect inspection systems 4 and 4'. Following the respective adjustment of the masks 1 and 1' on the defect inspection systems 4, 4', strips covering approximately 1000×1,000,000 pixels are started to be scanned on the defect inspection system 4. At the same time, the control computer 5 sends a signal via the interface 6 to the control computer 5' to initiate scanning of the corresponding strip on the mask 1' that has the same coordinates as the strip currently being scanned on the mask 1 in the defect inspection system 4.

The pixel data from the scanned image of the mask 1' that is inspected on the defect inspection system 4' is transmitted from the control computer 5' via the interface 6 to the control computer 5 of the first defect inspection system 4. On the control computer 5, there is an image processing program that compares the two scanned images with each other and signals the appropriate defect results to the operator that is looking after system.

While the image processing is still running, the control computer 5 starts the inspection of the next scanned sub-area on the mask 1 in the defect inspection system 4, and as described above, the corresponding signal is sent to the control computer 5' to start the inspection of the identical sub-area on the mask 1'.

For the image processing task, a further control computer 7 (See FIG. 3) connected via the bus system or interface 6 can also be used to relieve the load on the aforementioned control computers 5, and 5'. It is particularly advantageous that, if problems occur during the inspection of the sub-areas, the inspection can be interrupted immediately to examine the faults more accurately and in more detail or to initiate appropriate follow-up actions. This would not be possible in the case of massive temporary data storage when using only one defect inspection system.

Figure 3:
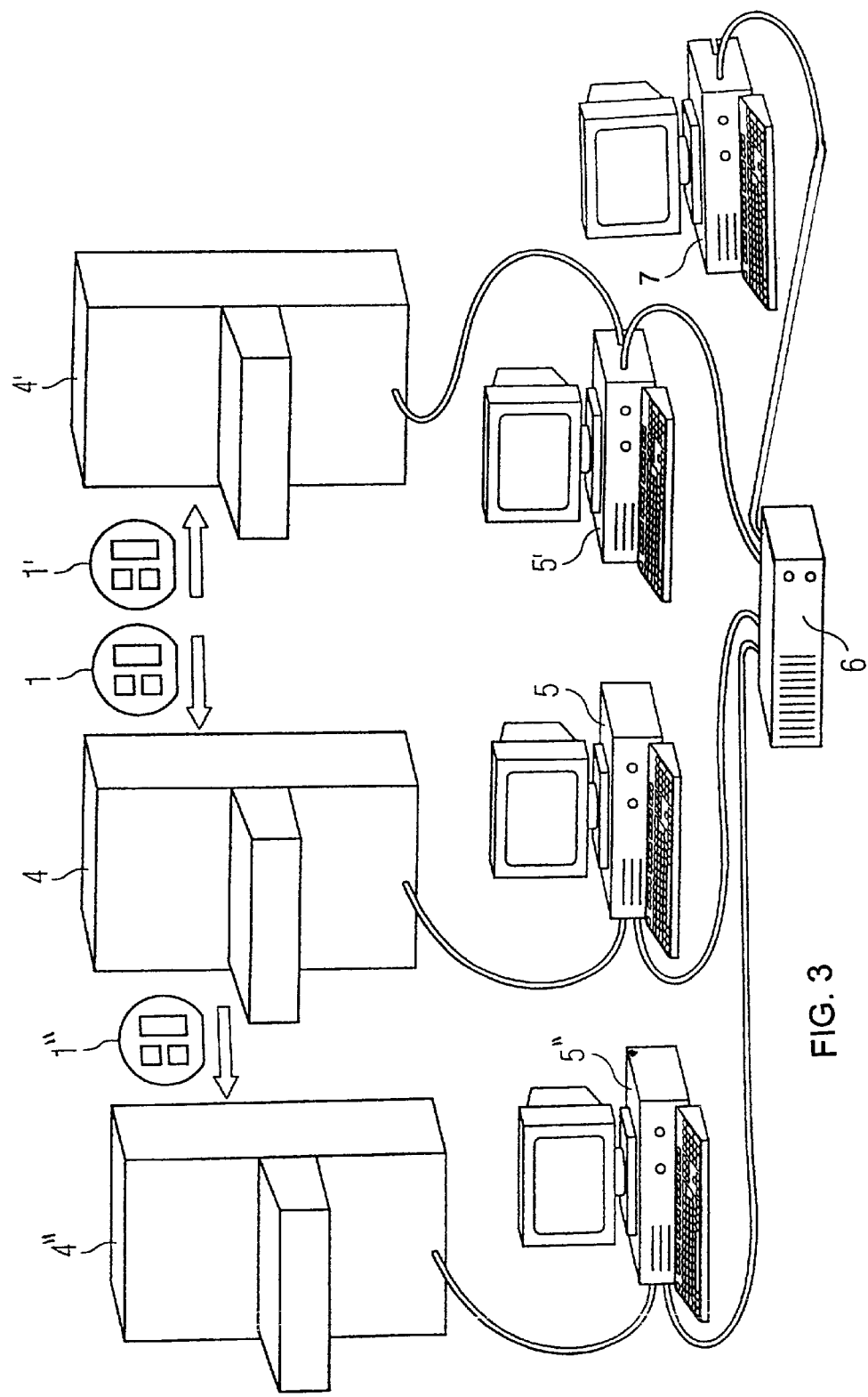
FIG. 3 schematically shows three interconnected defect inspection systems.

FIG. 3 shows an additional defect inspection system 4" with an associated control computer 5" that is connected to the interface 6. This measure allows the reference mask 1' to be used to inspect an additional mask 1" for defects. Similarly, a greater number of defect inspection systems can be connected together so that a greater number of masks can be simultaneously checked for defects using the reference mask 1'. As already explained, a further control computer 7 can be connected via the interface 6 to relieve the load on the control computers 5, 5', and 5".

I claim:

1. A method for inspecting defects on a mask, which comprises:
   (a) loading a first defect inspection system with a first mask having a surface with at least a sub-area having structuring;
   (b) loading a second defect inspection system with a reference mask having a surface with at least a sub-area having structuring that is identical to the structuring of the sub-area of the first mask;
   (c) connecting a bus system between a first control computer belonging to the first defect inspection system and a second control computer belonging to the second defect inspection system and using the bus system to communicate between the first control computer and the second control computer;
   (d) using the first defect inspection system to record a portion of the sub-area of the first mask and using the first control computer to construct a first image from the portion;

(e) using the second defect inspection system to record a portion of the sub-area of the reference mask and using the second control computer to construct a second image from the portion of the reference mask;

(f) using the bus system to perform an operation selected from the group consisting of transferring the first image from the first control computer to the second control computer and transferring the second image from the second control computer to the first control computer;

(g) comparing the first image with the second image; and (h) classifying the first mask based on a result of the comparing step.

2. The method according to claim 1, wherein after step (g), steps (d), (e) and (f) are repeated to record further portions of the sub-area of the first mask and of the sub-area of the reference mask.

3. The method according to claim 2, which comprises while inspecting the first mask, inspecting the reference mask.

4. The method according to claim 1, wherein step (g) is carried out while:
using the first defect inspection system to record another portion of the sub-area of the first mask and using the first control computer to construct a first image from the other portion; and
using the second defect inspection system to record another portion of the sub-area of the reference mask and using the second control computer to construct a second image from the other portion of the reference mask.

5. The method according to claim 1, which comprises providing the first mask as a mask structured on a silicon wafer and providing the reference mask as a mask structured on a silicon wafer.

6. The method according to claim 1, which comprises:
selecting the first mask from the group consisting of a mask structured on a silicon wafer and a mask structured on quartz plate with a reflective coating; and
selecting the reference mask from the group consisting of a mask structured on a silicon wafer and a mask structured on quartz plate with a reflective coating.

7. The method according to claim 1, which comprises outputting control signals from a control computer selected from the group consisting of the first control computer and the second control computer to control both the first defect inspection system and the second defect inspection system.

8. The method according to claim 1, which comprises using a bus system providing communication to connect at least a third control computer to the first control computer and to the second control computer.

9. The method according to claim 8, which comprises:
connecting at least a third defect inspection system to the third control computer; and
loading the third defect inspection system with a mask for inspection.

10. The method according to claim 1, which comprises while inspecting the first mask, inspecting the reference mask.

11. A method for inspecting defects on a mask, which comprises:
(a) loading a first defect inspection system with a first mask having a surface with at least a sub-area having structuring and singular structures within the sub-area;
(b) loading a second defect inspection system with a reference mask having a surface with at least a sub-area having structuring that is identical to the structuring of the sub-area of the first mask;

(c) connecting a bus system between a first control computer belonging to the first defect inspection system and a second control computer belonging to the second defect inspection system and using the bus system to communicate between the first control computer and the second control computer;

(d) using the first defect inspection system to record a portion of the sub-area of the first mask and using the first control computer to construct a first image from the portion;

(e) using the second defect inspection system to record a portion of the sub-area of the reference mask and using the second control computer to construct a second image from the portion of the reference mask;

(f) using the bus system to perform an operation selected from the group consisting of transferring the first image from the first control computer to the second control computer and transferring the second image from the second control computer to the first control computer;

(g) comparing the first image with the second image; and (h) classifying the first mask based on a result of the comparing step.

12. The method according to claim 11, wherein after step (g), steps (d), (e) and (f) are repeated to record further portions of the sub-area of the first mask and of the sub-area of the reference mask.

13. The method according to claim 12, which comprises while inspecting the first mask, inspecting the reference mask.

14. The method according to claim 11, wherein step (g) is carried out while:
using the first defect inspection system to record another portion of the sub-area of the first mask and using the first control computer to construct a first image from the other portion; and
using the second defect inspection system to record another portion of the sub-area of the reference mask and using the second control computer to construct a second image from the other portion of the reference mask.

15. The method according to claim 11, which comprises providing the first mask as a mask structured on a silicon wafer and providing the reference mask as a mask structured on a silicon wafer.

16. The method according to claim 11, which comprises:
selecting the first mask from the group consisting of a mask structured on a silicon wafer and a mask structured on quartz plate with a reflective coating; and
selecting the reference mask from the group consisting of a mask structured on a silicon wafer and a mask structured on quartz plate with a reflective coating.

17. The method according to claim 11, which comprises outputting control signals from a control computer selected from the group consisting of the first control computer and the second control computer to control both the first defect inspection system and the second defect inspection system.

18. The method according to claim 11, which comprises using a bus system providing communication to connect at least a third control computer to the first control computer and to the second control computer.

19. The method according to claim 18, which comprises:
connecting at least a third defect inspection system to the third control computer; and
loading the third defect inspection system with a mask for inspection.

20. The method according to claim 11, which comprises while inspecting the first mask, inspecting the reference mask.

* * * * *